(12) United States Patent
Vreeke et al.

(10) Patent No.: US 7,163,616 B2
(45) Date of Patent: Jan. 16, 2007

(54) REAGENTS AND METHODS FOR DETECTING ANALYTES, AND DEVICES COMPRISING REAGENTS FOR DETECTING ANALYTES

(75) Inventors: Mark S. Vreeke, Houston, TX (US); Mary Ellen Warchal-Windham, Osceola, IN (US); Christina Blaschke, White Pigeon, MI (US); Barbara J. Mikel, Mishawaka, IN (US); Howard A. Cooper, Elkhart, IN (US)

(73) Assignee: Bayer Corporation, Elkhart, IN (US)

( * ) Notice: Subject to any disclaimer, the term of this patent is extended or adjusted under 35 U.S.C. 154(b) by 102 days.

(21) Appl. No.: 10/231,539

(22) Filed: Sep. 3, 2002

(65) Prior Publication Data

US 2003/0094384 A1  May 22, 2003

Related U.S. Application Data

(60) Provisional application No. 60/318,716, filed on Sep. 14, 2001.

(51) Int. Cl.
   *G01N 27/327* (2006.01)
(52) U.S. Cl. ............................ 205/777.5; 204/403.14
(58) Field of Classification Search ............... 204/403, 204/409, 412, 403.14; 205/775, 777.5; 435/14, 435/25, 26, 810, 817; 436/806, 808, 149, 436/151
See application file for complete search history.

(56) References Cited

U.S. PATENT DOCUMENTS

| 4,545,382 A | 10/1985 | Higgins et al. ............. 128/635 |
| 4,711,245 A | 12/1987 | Higgins et al. ............. 128/635 |
| 4,863,016 A | 9/1989 | Fong et al. .................. 206/210 |
| 4,941,308 A | 7/1990 | Grabenkort et al. .......... 53/425 |
| 5,120,420 A | 6/1992 | Nankai et al. ............... 204/403 |
| 5,206,147 A | 4/1993 | Hoenes ........................ 435/25 |
| 5,212,092 A | 5/1993 | Jackson et al. ............... 436/11 |
| 5,236,567 A | 8/1993 | Nanba et al. ................ 204/403 |

(Continued)

FOREIGN PATENT DOCUMENTS

EP    0 330 517 A    8/1989

(Continued)

OTHER PUBLICATIONS

Taylor, C.; Kenausis, G.; Katakis, I.; Heller, A.; "Wiring" of glucose oxidase within a hydrogel made with polyvinyl imidazole complexed with [Ox-4,4'-dimethoxy-2,2'-bipyridin)CI]+/2+, Journal of Electroanalytical Chemistry, 1995, vol. 396, pp. 511-515.*

(Continued)

*Primary Examiner*—Kaj K. Olsen
(74) *Attorney, Agent, or Firm*—Jenkens & Gilchrist

(57) ABSTRACT

Reagents for detecting an analyte are described. A reagent comprises (a) an enzyme selected from the group consisting of a flavoprotein, a quinoprotein, and a combination thereof; and (b) a mediator selected from the group consisting of a phenothiazine, a phenoxazine, and a combination thereof. In addition, reagents having good stability to radiation sterilization are described. Electrochemical sensors and sampling devices comprising such reagents, methods of producing a sterilized device including such reagents, and methods for detecting an analyte which utilize such reagents are described as well.

40 Claims, 6 Drawing Sheets

Layer 1    Layer 2    Layer 3

Laminated Structure

U.S. PATENT DOCUMENTS

| | | | | |
|---|---|---|---|---|
| 5,298,144 | A | | 3/1994 | Spokane .................. 204/403 |
| 5,334,508 | A | | 8/1994 | Hoenes ....................... 435/25 |
| 5,393,615 | A | | 2/1995 | Corey et al. ................. 429/43 |
| 5,411,647 | A | * | 5/1995 | Johnson et al. .......... 205/777.5 |
| 5,520,786 | A | * | 5/1996 | Bloczynski et al. ... 204/403.14 |
| 5,798,031 | A | | 8/1998 | Charlton et al. ............. 204/403 |
| 5,801,057 | A | | 9/1998 | Smart et al. .................. 436/68 |
| 6,057,120 | A | | 5/2000 | Heindl et al. ................. 435/25 |
| 6,299,757 | B1 | * | 10/2001 | Feldman et al. ............ 205/775 |
| 6,773,564 | B1 | * | 8/2004 | Yugawa et al. ........ 204/403.14 |

FOREIGN PATENT DOCUMENTS

| | | |
|---|---|---|
| EP | 1 130 111 A | 9/2001 |
| WO | WO 92 07263 A | 4/1992 |
| WO | WO 92 07953 A | 5/1992 |

OTHER PUBLICATIONS

Olsthoorn, Arjen. "Structural and Mechanistic Aspects of Soluble Quinoprotein Glucose Dehydrogenase from *Acinetobacter calcoaceticus*"; Ph.D. Dissertation, Delft University of Technology, The Netherlands; 1999; pp. i-vi, 1-69.

Dewanti, Asteriani Ratih; "Enzymology of Quinoprotein Glucose Dehydrogenases from *Acinetobacter calcoaceticus*"; Ph.D. Dissertation, Delft University of Technology, The Netherlands; 2000; pp. i-viii, 1-107.

Abstract of JP6114041A2 (issued Apr. 26, 1994): Jackson, Jeffrey T.; Hui, Henry K. "Storage and Calibration Solution for Blood Gas Sensor Device of Blood in Multi-Charateristic Value Blood Vessel"; pp. 1-2.

Abstract of JP3180750A2 (issued Aug. 6, 1991): Yamaguchi, Hideichiro. "Cell for Chemical Sensor and Chemical Sensor Having This Cell"; pp. 1-2.

Abstract of JP7083870A2 (issued Mar. 31, 1995): Kojima, Naomi; Sugama, Akio; Suzuki, Hiroaki. "Sterilization Method for Enzyme Film"; pp. 1-2.

Abstracts from ISI Current Contents, 1992-1999; 306 records.

* cited by examiner

Layer 1  Layer 2  Layer 3

Laminated
Structure

REAGENTS AND METHODS FOR DETECTING ANALYTES, AND DEVICES COMPRISING REAGENTS FOR DETECTING ANALYTES

This application claims benefit to provisional application 60/318,716, filed on Sep. 14, 2001.

BACKGROUND

The present invention relates to reagents, methods and devices for measurement of analytes and, more particularly, to reagents, methods and devices for the measurement of glucose in the blood.

The monitoring of certain analyte concentrations in the body enables early detection of health risks, and identifies the need for the introduction of therapeutic measures. One of the most commonly monitored analytes is glucose, the blood concentration of which is important in determining the appropriate dosages of insulin for diabetics. Various methods have been developed for monitoring glucose levels in the blood, including the use of electrochemical biosensors. Electrochemical biosensors are based on enzyme-catalyzed chemical reactions involving the analyte of interest. In the case of glucose monitoring, the relevant chemical reaction is the oxidation of glucose to gluconolactone. This oxidation is catalyzed by a variety of enzymes, some of which may contain a bound coenzyme such as nicotinamide adenine dinucleotide (phosphate) (NAD(P)), while others may contain a bound cofactor such as flavin adenine dinucleotide (FAD) or pyrroloquinolinequinone (PQQ).

In biosensor applications, the redox equivalents generated in the course of the oxidation of glucose are transported to the surface of an electrode whereby an electrical signal is generated. The magnitude of the electrical signal is then correlated with concentration of glucose. The transfer of redox equivalents from the site of chemical reaction in the enzyme to the surface of the electrode is accomplished with the use of electron transfer mediators.

A significant problem with the use of electron transfer mediators in biosensors is the instability of these compounds upon exposure to common environmental conditions such as temperature and moisture. As a result, the number of mediators suitable for use in glucose biosensors is quite limited.

U.S. Pat. No. 5,520,786 ('786) to Bloczynski et al. describes families of phenothiazine and phenoxazine compounds suitable for use as electron transfer mediators with the enzymes dihydronicotinamide adenine dinucleotide (NADH), NADPH, and analogs thereof. Cofactor based enzymes such as FAD-glucose oxidase and PQQ-glucose dehydrogenase have several advantages over NAD-based enzymes, including lower cost, higher enzyme activity, increased stability, and bound as opposed to readily dissociable cofactor.

Electron transfer mediators previously used with FAD-glucose oxidase and PQQ-glucose dehydrogenase include quinones, phenzine methosulfate, dichlorophenolindophenol and ferricyanide. Unfortunately, these compounds have proven to be highly susceptible to the environmental agents described above, and result in biosensor reagents of low stability. Thus, mediators are needed which exhibit good stability upon exposure to commonly-encountered environmental agents, and which can be used in flavoprotein- and quinoprotein-based systems.

In addition to the need for biosensor reagents that are stable to the environmental agents described above, it would be desirable to provide biosensor reagents that are stable to the radiation conditions commonly employed in lancet sterilization. Reagents stable to such radiation sterilization could be incorporated into highly user-convenient units in which lancet and biosensor are combined.

The present invention is directed to electron transfer mediators for use in flavoprotein- and quinoprotein-based biosensor reagents, which exhibit improved stability to both environmental interferents and to radiation sterilization.

SUMMARY

The scope of the present invention is defined solely by the appended claims, and is not affected to any degree by the statements within this summary. By way of introduction, the presently preferred embodiments described herein are directed towards remedying the aforementioned stability problems of electron transfer mediators and enzyme biosensors.

Briefly stated, a composition aspect of the present invention is directed to a reagent for detecting an analyte, comprising (a) an enzyme selected from the group consisting of a flavoprotein, a quinoprotein, and a combination thereof; and (b) a mediator selected from the group consisting of a phenothiazine, a phenoxazine, and a combination thereof.

A first apparatus aspect of the present invention is directed to an electrochemical sensor comprising: (a) a working electrode having a surface; and (b) a second electrode coupled to the working electrode. The surface of the working electrode is coated with a solution or mixture of a reagent comprising an enzyme selected from the group consisting of a flavoprotein, a quinoprotein, and a combination thereof; and a mediator selected from the group consisting of a phenothiazine, a phenoxazine, and a combination thereof.

A second apparatus aspect of the present invention is directed to a device for measuring an analyte, comprising (a) a lancet; and (b) a sampling chamber connected to the lancet. The sampling chamber comprises a reagent comprising an enzyme selected from the group consisting of PQQ-glucose dehydrogenase, FAD-glucose oxidase, and a combination thereof; and (b) a mediator selected from the group consisting of a phenothiazine, a phenoxazine, and a combination thereof.

A first method aspect of the present invention is directed to a method of producing a sterilized device for measuring an analyte, comprising (a) providing a device in accordance with the present invention, and (b) irradiating the device with E-beam or gamma ray radiation.

A second method aspect of the present invention is directed to a method for detecting an analyte which undergoes a chemical reaction, the method comprising (a) providing an electrode surface; (b) catalyzing the chemical reaction with an enzyme selected from the group consisting of a flavoprotein, a quinoprotein, and a combination thereof; (c) generating a redox equivalent by the chemical reaction; and (d) transferring the redox equivalent to the electrode surface using a mediator selected from the group consisting of a phenothiazine, a phenoxazine, and a combination thereof.

The presently preferred embodiments discussed herein may possess one or more advantages relative to other flavoprotein- and quinoprotein-based biosensor reagents, which can include but are but not limited to: improved biosensor reagent stability; enhanced electron transfer capability of mediators; ability to tune mediators for optimum electrode operation; reduced oxygen susceptibility of mediators; increased thermal stability of mediators; increased stability of mediators to ambient humidity; lower redox potential of mediators; reduced susceptibility to interferents in blood; and stability of biosensor reagents to radiation sterilization conditions.

DETAILED DESCRIPTION OF THE PRESENTLY PREFERRED EMBODIMENTS

Figure 1:
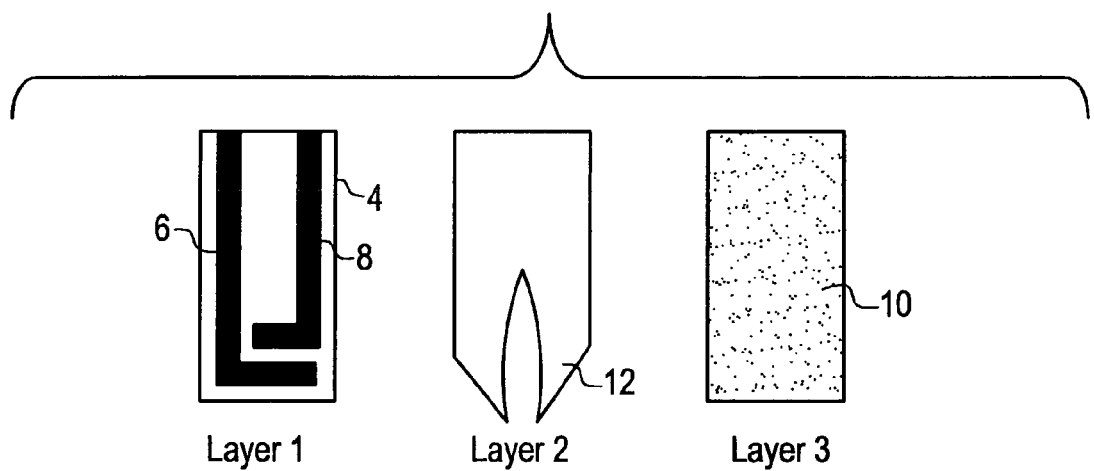
FIG. 1 shows a schematic illustration of a device for measuring an analyte that embodies features of the present invention.
Figure 1:
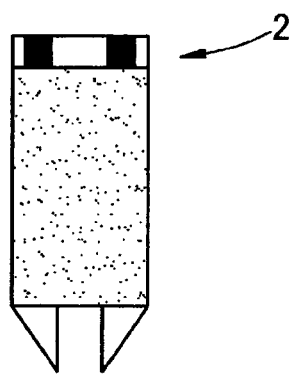

Throughout this description and in the appended claims, the following definitions are to be understood: The term "analyte" refers to one or a plurality of species having a concentration of interest. The term "flavoprotein" refers to enzymes containing flavin cofactors. The term "quinoprotein" refers to enzymes containing PQQ or similar cofactors. The phrase "redox equivalent" refers to one or a plurality of charged species (e.g., electrons) produced in electrochemical reactions involving the analyte. The phrase "E-beam irradiation" or "electron beam irradiation" refers to a process of exposure to a concentrated, high-current stream of electrons. The terms "alkyl," "alkenyl," "alkynyl," "aryl," "heteroaryl," "cyclic," "heterocyclic," "halo," "haloalkyl," "carboxy," "carboxyalkyl," "alkoxycarbonyl," "aryloxycarbonyl," "aromatic keto," "aliphatic keto," "alkoxy," "aryloxy," "nitro," "dialkylamino," "aminoalkyl," "sulfo," "dihydroxyboron," and the like refer to substituents well known in the art, which may be branched or unbranched and may themselves be substituted with one or more substituents. The phrase "biosensor reagent" refers to the combination of an enzyme that catalyzes a reaction of an analyte, and a phenothiazine and/or phenoxazine mediator. The term "bioburden" refers to the population of viable microorganisms on a product determined immediately prior to irradiation.

A biosensor reagent for detecting an analyte in accord with the present invention includes (1) an enzyme selected from the group consisting of a flavoprotein, a quinoprotein, and a combination thereof; and (2) a mediator selected from the group consisting of a phenothiazine, a phenoxazine, and a combination thereof.

The nature of the analyte monitored in accord with the present invention is unrestricted, provided the analyte undergoes a chemical reaction that is catalyzed by an enzyme selected from the group consisting of a flavoprotein, a quinoprotein, and a combination thereof. Preferred analytes include but are not limited to glucose, lactate, D-amino acids, ascorbate, alcohol, cholesterol, choline, and acetylcholine.

Flavoproteins in accord with the present invention include FAD-glucose oxidase (Enzyme Classification No. 1.1.3.4), Flavin-hexose oxidase (EC No. 1.1.3.5) and FAD-glucose dehydrogenase (EC No. 1.1.99.10) For information relating to these flavoproteins, see: Adriaan Joseph Jan Olsthoorn, "Structural and Mechanistic Aspects of Soluble Quinoprotein Glucose Dehydrogenase from *Acinetobacter calcoaceticus*," Ph.D. dissertation, Delft University of Technology, The Netherlands, 1999. Additional oxidase enzymes for use in accord with the present invention include but are not limited to lactate oxidase, cholesterol oxidase, alcohol oxidase (e.g., methanol oxidase), d-aminoacid oxidase, choline oxidase, and FAD derivatives thereof. A preferred flavoprotein for use in accord with the present invention is FAD-glucose oxidase.

Quinoproteins in accord with the present invention include but are not limited to membrane bound and soluble PQQ-glucose dehydrogenase (EC No. 1.1.99.17). Information relating to PQQ-glucose dehydrogenase can be found in the Olsthoorn reference cited above. Additional quinoprotein enzymes for use in accord with the present invention include but are not limited to lactate dehydrogenase, aldehyde dehydrogenase, methylamine dehydrogenase, alcohol dehydrogenase (e.g., methanol dehydrogenase), and PQQ derivatives thereof. A preferred quinoprotein for use in accord with the present invention is PQQ-glucose dehydrogenase.

Mediators in accord with the present invention include phenothiazines having the formula

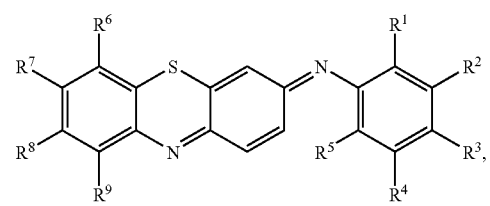

and phenoxazines having the formula

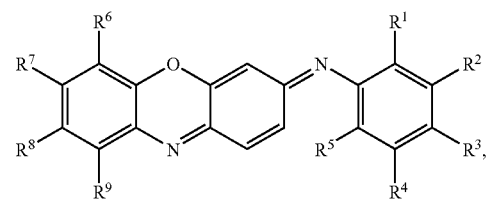

wherein $R^1$, $R^2$, $R^3$, $R^4$, $R^5$, $R^6$, $R^7$, $R^8$, and $R^9$ are the same or different, and are independently selected from the group consisting of hydrogen, alkyl, alkenyl, alkynyl, aryl, heteroaryl, cyclic, heterocyclic, halo, haloalkyl, carboxy, carboxyalkyl, alkoxycarbonyl, aryloxycarbonyl, aromatic keto, aliphatic keto, alkoxy, aryloxy, nitro, dialkylamino, aminoalkyl, sulfo, dihydroxyboron, and combinations thereof.

In contrast to the single electron transfer carrying capability of $K_3Fe(CN)_6$, mediators in accord with the present invention have the ability to carry two redox equivalents, and are therefore well suited for use in FAD and quinoprotein oxidation/reduction processes, which generally involve the transfer of two electrons. Moreover, the potential of mediators of the present invention can be tuned to the optimum potential (i.e., the potential where the signal contribution from interferences is minimized) for a specific sample matrix by varying the substitution on the aromatic rings. Electron-donating substituents (e.g., alkyl, alkoxy, amine, hydroxy, etc.) result in decreased redox potentials, while electron-withdrawing substituents (e.g., carboxylic acid, ester, aldehyde, ketone, nitrile, nitro, sulfonic acid, trifluromethyl, etc.) result in increased redox potentials. For blood or plasma samples, the ideal potential usually lies between about −200 and about 100 mV versus an Ag/AgCl reference.

The substituents on the aromatic rings, in addition to their utility in tuning the redox potentials of the mediators, can also be used to enhance mediator solubility. For example, the introduction of a substituent having the capacity for hydrogen bonding can be expected to render the mediator more water soluble than a mediator lacking such substitution. In addition, these substituents can serve as functional groups for immobilizing the mediators to a support (e.g., the electrode surface or, alternatively, a chemical matrix such as a polymer backbone, which is suitable for application to the electrode surface).

Preferably, mediators used in biosensor reagents according to the present invention include 3-(4'-chloro-phenylimino)-3H-phenothiazine, 3-(4'-diethylamino-phenylimino)-3H-phenothiazine, 3-(4'ethyl-phenylimino)-3H-phenothiazine, 3-(4'-trifluoromethyl-phenylimino)-3H-phenothiazine, 3-(4'-methoxycarbonyl-phenylimino)-3H-phenothiazine, 3-(4'-nitro-phenylimino)-3H-phenothiazine, 3-(4'-methoxy-phenylimino)-3H-phenothiazine, 7-acetyl-3-(4'-methoxycarbonylphenylimino)-3H-phenothiazine, 7-trifluoromethyl-3-(4'-methoxycarbonylphenylimino)-3H-phenothiazine, 3-(4'-ω-carboxy-n-butyl-phenylimino)-3H-phenothiazine, 3-(4'-aminomethyl-phenylimino)-3H-phenothiazine, 3-(4'-(2"-(5"-(p-aminophenyl)-1,3,4-oxadiazoyl)phenylimino)-3H-phenothiazine, 3-(4'-β-aminoethyl-phenylimino)-3H-phenothiazine, 6-(4'-ethylphenyl)amino-3-(4'-ethyl-phenylimino)-3H-phenothiazine, 6-(4'-[2-(2-ethanoloxy)ethoxy]ethoxyphenyl)amino-3-(4'-[2-(2-ethanoloxy)ethoxy]ethoxy-phenylimino-3H-phenothiazine, 3-(4'-[2-(2-ethanoloxy)ethoxy]ethoxy-phenylimino-3H-phenothiazine, 3-(4'-phenylimino)-3H-phenothiazineboronic acid, (3-(3',5'-dicarboxy-phenylimino)-3H-phenothiazine, 3-(4'-carboxy-phenylimino)-3H-phenothiazine, 3-(3',5'-dicarboxy-phenylimino)-3H-phenoxazine, 3-(3',5'-phenylimino)-3H-phenothiazinedisulfonic acid, and 3-(3-phenylimino)-3H-phenothiazinesulfonic acid.

More preferably, the mediator used in accord with the present invention is selected from the group consisting of

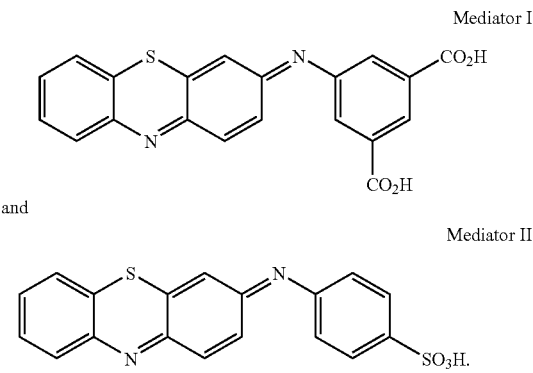

Mediator I and

Mediator II

Relative to ferricyanide, phenothiazine mediators—in particular mediator I—are less susceptible to oxygen degradation, more thermally stable, and more stable to ambient humidity. In addition, mediator I works at a lower redox potential than ferricyanide. For example, $E_0$ for mediator I is approximately 0 mV versus an Ag/AgCl reference, whereas $E_0$ for ferricyanide is approximately 250 mV versus an. Ag/AgCl reference. The lower redox potential of phenothiazine mediators is advantageous in that there is a region around 0 mV versus an Ag/AgCl reference in which the amount of electrochemical interferences are minimized. Thus, the impact from chemical interferents in the blood can be minimized by using these mediators.

Reagents embodying features of the present invention can be incorporated into a variety of biosensor devices, including but not limited to the ones described in U.S. Pat. No. 5,120,420 and U.S. Pat. No. 5,798,031, the entire contents of both of which are incorporated herein by reference, except that in the event of any inconsistent disclosure or definition from the present application, the disclosure or definition herein shall be deemed to prevail.

Turning now to the drawings, FIG. 1 shows a representative electrochemical sensor in accordance with the present invention. The electrochemical sensor 2 is comprised of an insulating base 4 upon which is printed (typically by screen printing techniques) an electrode pattern (6 and 8) and a reagent layer 10 that contains a reagent embodying features of the present invention. The two parts of the electrode print, 6 and 8, provide the working and reference electrodes necessary for the electrochemical determination. A lancet element 12 can be incorporated into the electrochemical sensor (e.g., interposed between layers 1 and 2), as is described more fully hereinbelow. The three layers shown in FIG. 1 can be joined by means of an adhesive (e.g., pressure sensitive, hot melt, etc.) or by sonic welding, depending on the identity of the materials.

Figure 2:
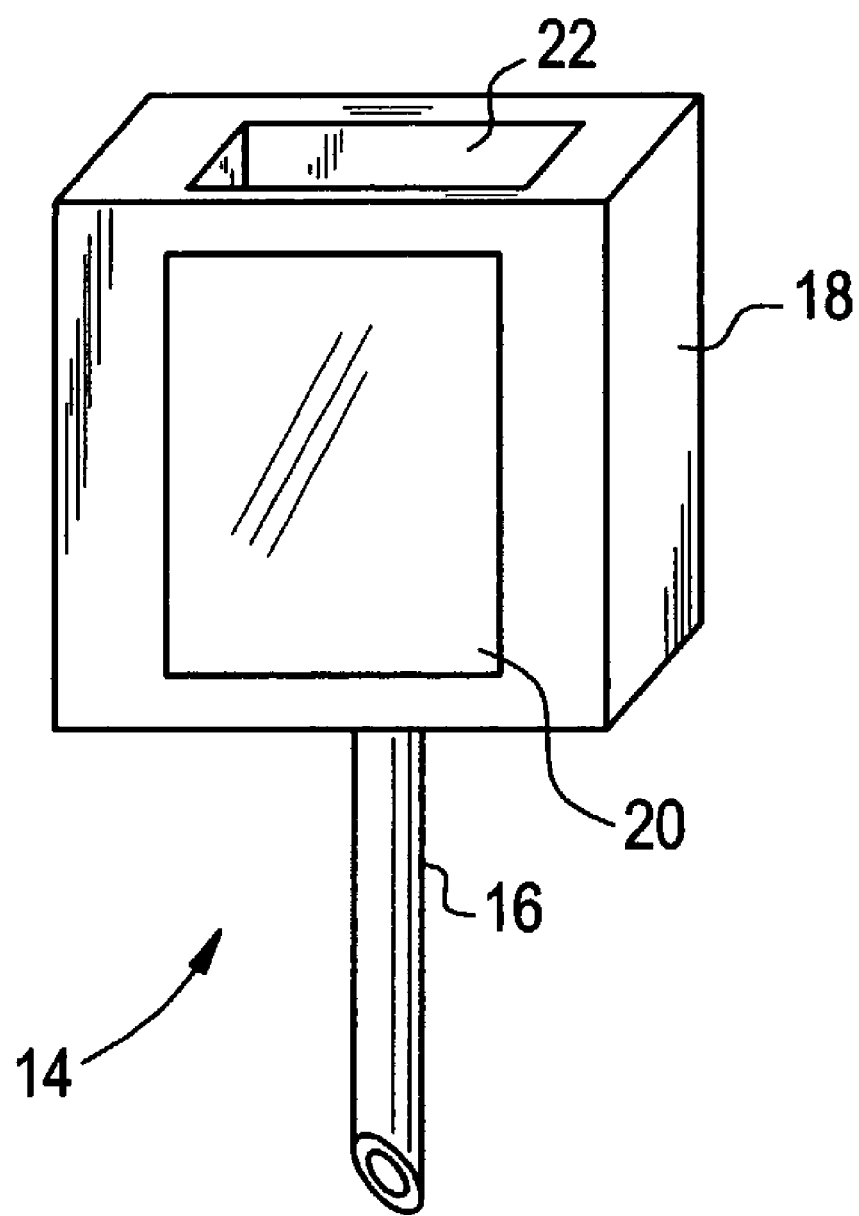
FIG. 2 shows a perspective view of an integrated lancet/biosensor device for use in accordance with the present invention.

It has been found that biosensor reagents comprising PQQ-glucose dehydrogenase and certain phenothiazine mediators exhibit high stability to radiation sterilization. A preferred application of radiation stable biosensor reagents in accord with the present invention is for the development of integrated lancet/biosensor devices. An example of such an integrated device is illustrated in FIG. 2 and described in U.S. Pat. No. 5,801,057, the entire contents of which are incorporated herein by reference, except that in the event of any inconsistent disclosure or definition from the present application, the disclosure or definition herein shall be deemed to prevail.

As shown in FIG. 2, the integrated lancet/biosensor device 14 has a finely bored needle 16 connected to a sampling chamber 18. Sampling chamber 18 has at least one optical window 20 and a vent 22 through which air can be displaced when the chamber 18 fills with blood or other fluids. Preferably, sampling chamber 18 comprises a biosensor reagent comprising PQQ-glucose dehydrogenase and a phenothiazine and/or phenoxazine mediator. Preferably, the mediator is a phenothiazine. More preferably, the mediator has a structure represented by mediator I or mediator II above. Once sampling chamber 18 has been loaded with biosensor reagent, the entire device 14 can be subjected to radiation sterilization. Preferably, the method of sterilization involves electron beam (E-beam) irradiation or gamma irradiation.

As set forth in the Association for the Advancement of Medical Instrumentation document ANSI/AAMI/ISO 11137-1994, products that penetrate the skin and come into contact with the blood must have a sterility assurance level (SAL) of $10^{-6}$, which corresponds to a one in a million probability of a viable microorganism being present on a product unit after sterilization. The sterilization dose needed to achieve a $10^{-6}$ SAL depends on the bioburden of the sample. For example, a sample with a bioburden of 1,021 requires a sterilization dose of 24.9 kGy to achieve a $10^{-6}$ SAL.

In the examples described hereinbelow, electron beam (E-beam) irradiation was employed as the method of sterilization. The biosensor reagents subjected to the electron beam absorb energy from the electrons. The energy that is absorbed per unit mass of material is referred to as the absorbed dose, and it is this absorption of energy—or dose delivery—that destroys the reproductive cells and DNA chains of microorganisms, thereby rendering a product sterile. E-beam doses of 25, 50 and 100 kGy were used because the bioburden of the biosensor reagents was unknown.

Figure 3:
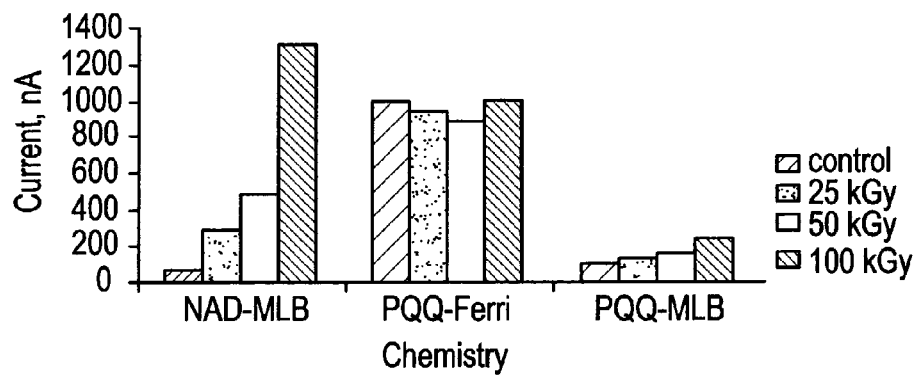
FIG. 3 shows a graph of background currents for 3 formulations of biosensor reagents exposed to increasing levels of radiation.
Figure 4:
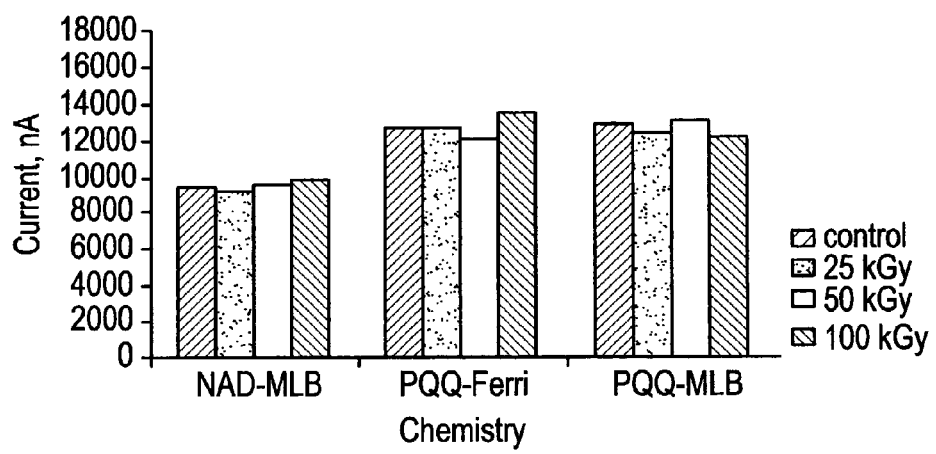
FIG. 4 shows a graph of the current response of radiation sterilized biosensor reagents upon exposure to glucose.

FIG. 3 shows a graph of the background currents observed for three formulations of biosensor reagents exposed to increasing levels of radiation: (1) NAD-glucose dehydrogenase with Mediator I, (2) PQQ-glucose dehydrogenase with Ferricyanide, and (3) PQQ-glucose dehydrogenase with Mediator I. The PQQ formulations tolerated the irradiation extremely well. In contrast, the NAD formulation exhibited poor tolerance to the sterilization conditions, and resulted in a background signal which constituted a significant amount of the glucose signal. While formulation (2) exhibited good tolerance to the radiation process, the activity of the extracted enzyme was lower than the corresponding activity of the enzyme extracted from formulation (3). FIG. 4 shows a graph of current response when these radiation-sterilized sensors were exposed to 600 mg/dL glucose.

The manner in which a device embodying features of the present invention is made, and the process by which such a device is used for monitoring an analyte, will be abundantly clear to one of ordinary skill in the art based upon joint consideration of both the preceding description, and the following representative procedures. It is to be understood that many variations in the presently preferred embodiments illustrated herein will be obvious to one of ordinary skill in the art, and remain within the scope of the appended claims and their equivalents.

For example, the working electrode employed in electrochemical sensors according to the present invention can be varied, with suitable electrodes including but not limited to carbon electrodes, platinum electrodes, palladium electrodes, gold electrodes, and the like. Similarly, the reference electrode can be varied, with suitable electrodes including but not limited to silver—silver chloride electrodes, calomel electrodes, saturated calomel electrodes, and the like. Alternatively, a quasi-reference electrode (e.g., a large surface area platinum electrode) of the type commonly used in non-aqueous electrochemical experiments (i.e., an electrode which does not have a specific redox species to which its potential is referenced) can be used in accord with the present invention. The surface areas of all electrodes employed in accordance with the present invention are likewise subject to variation. Preferably, the working electrode has dimensions of about 0.6 mm×1.2 mm.

Furthermore, the compositions and pH of the buffer solutions employed, and the enzyme activities and concentrations of components of the biosensor reagents, are subject to wide variation. Suitable buffer solutions include but are not limited to HEPES (i.e., N-2-hydroxyethylpiperazine-N'-2-ethanesulfonic acid), MOPS (i.e., 3-(N-morpholino)propanesulfonic acid), TES (i.e., N-tris(hydroxymethyl)methyl-2-aminoethanesulfonic acid), 2-([2-hydrox-1,1-bis(hydroxymethyl)-ethyl]amino)ethanesulfonic acid), PIPES (i.e., piperazine-N,N'-bis(2-ethanesulfonic acid)), 1,4-piperazinediethanesulfonic acid), ACES (i.e., N-(carbamoylmethyl)-2-aminoethanesulfonic acid), N-(2-acetamidol)-2-aminoethanesulfonic acid, BES (i.e., N,N-bis(2-hydroxyethyl)-2-aminoethanesulfonic acid, and Dulbecco's buffer (i.e., 0.008M sodium phosphate, 0.002M potassium phosphate, 0.14M sodium chloride, 0.01M potassium chloride, pH 7.4).

The manner in which reagents and devices embodying features of the present invention are made, and the methods by which these reagents and devices are used for monitoring an analyte, will be abundantly clear to one of ordinary skill in the art based upon joint consideration of both the preceding description, and the following representative procedures.

While the examples provided hereinbelow relate to in vitro applications of the biosensor reagents in accord with the present invention, it is contemplated that these reagents can also be adapted for in vivo analyte monitoring by chemically immobilizing the phenoxazine and/or phenothiazine mediators (e.g., by chemical reaction at one or more of the substituent groups on the aromatic rings), and incorporating the immobilized mediators into a device which can be implanted subcutaneously into a patient.

EXAMPLES

Preparation of Biosensor and Glucose Dose-Response

A liquid chemistry reagent was prepared to be 20 Units/µL pyrolloquinolinequinone-glucose dehydrogenase (PQQ-GDH) and 24 mM mediator I in 100 mM Sodium Phosphate, pH 7.4. The first component of the reagent was made by dissolving the mediator in 100 mM phosphate pH 7.4, adjusting the pH back to 7.4, and filtering the solution by forcing it through a Whatman 0.45 micron PTFE syringe filter. The reagent was completed by adding lyophilized PQQ-GDH (Toyobo Product No. GLD-321) to an activity of 20 U/µL.

The chemistry formulation was deposited onto electrodes, which had been produced using a 3-pass screen-printing process by Conductive Technologies, Inc. During this process, the silver/silver chloride (DuPont 5870 ink) leads and reference electrode were printed first onto polycarbonate base material. The second pass of Dupont 7102T carbon-graphite working electrode was printed on top of this. A final pass of Norcote RDMSK4954-A2 dielectric defined the working electrode area to be 0.0113 $cm^2$.

The chemistry was deposited over the working electrode with the use of an Asymtek Automove® 402 Dispensing System. The system was programmed to perform the transfer by dipping a 62 mL stainless steel pin into a 1.5 mL Eppendorf vial filled with reagent. Polycarbonate lid material was laminated to the sensors creating a capillary area over the working and reference electrodes capable of holding approximately 3 μL of test solution. The capillary area, which defines the sample volume, is first formed in the polycarbonate lid material by a coining or stamping process.

Figure 5:
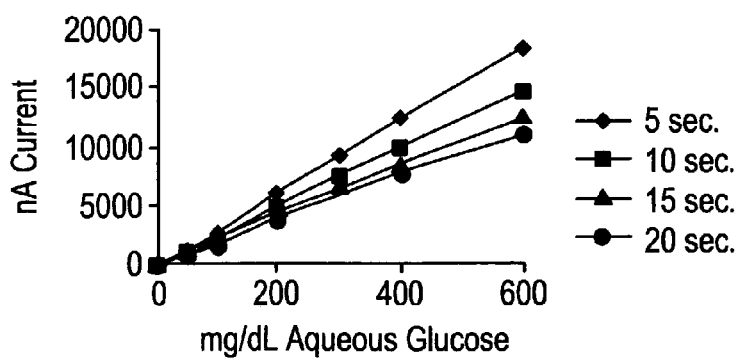
FIG. 5 shows a plot of current vs. glucose concentration at increasing time intervals for a PQQ-glucose dehydrogenase/phenothiazine biosensor.

As shown in FIG. 5, reactivity of the chemistry was analyzed by generating a glucose dose-response curve with buffered (100 mM phosphate, 100 mM sodium chloride, pH 7.4) samples containing a range of glucose concentrations from 0 to 600 mg/dL. Current generated at each of the glucose concentrations was measured using a potentiostat programmed to apply 150 mV potential with trigger level set to 100 nA, and timing programmed to record the current at 5, 10, 15, and 20 seconds. The trigger level refers to a threshold level above which timing and recording are initiated.

Figure 6:
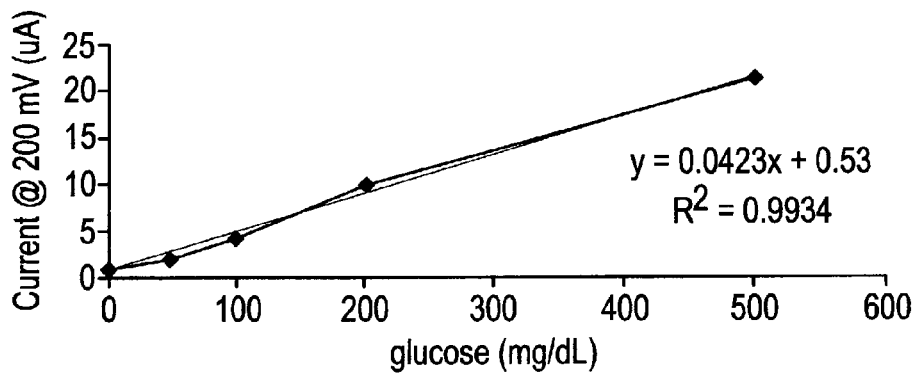
FIG. 6 shows a plot of current vs. glucose concentration for a [FAD]-glucose oxidase/phenothiazine biosensor.

Sensors formulated with 20U Glucose Oxidase/sensor and 6 mM mediator I were deposited onto electrode sensors as above. The dose response plot shown in FIG. 6 was obtained.

Preparation of Electrochemical Biosensor and Heat/Humidity Stability

Electrochemical biosensors were constructed using a screen-printing process. Sensors were comprised of a carbon working electrode and a silver/silver chloride reference electrode. A solution (150 to 800 nl) containing 12 mM mediator I in 100 mM phosphate buffer (pH 7.4), and of the enzyme PQQ-glucose dehydrogenase (10 U/μL) was deposited on the surface of the working electrode and allowed to dry at room temperature for 5 minutes prior to desiccation. The electrodes were assembled into a format having a small capillary gap, which allowed inoculation of the sensors with sample solutions.

Figure 7:
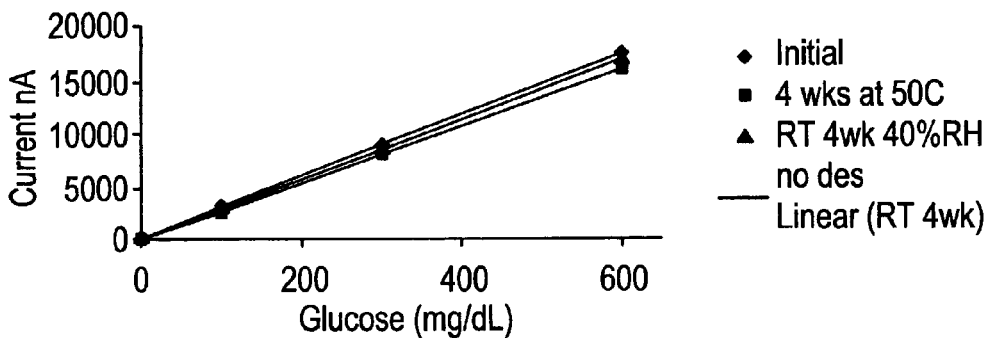
FIG. 7 shows a plot of current vs. glucose concentration for a PQQ-glucose dehydrogenase/phenothiazine biosensor reagent subjected to heat stress and humidity stress.
Figure 8:
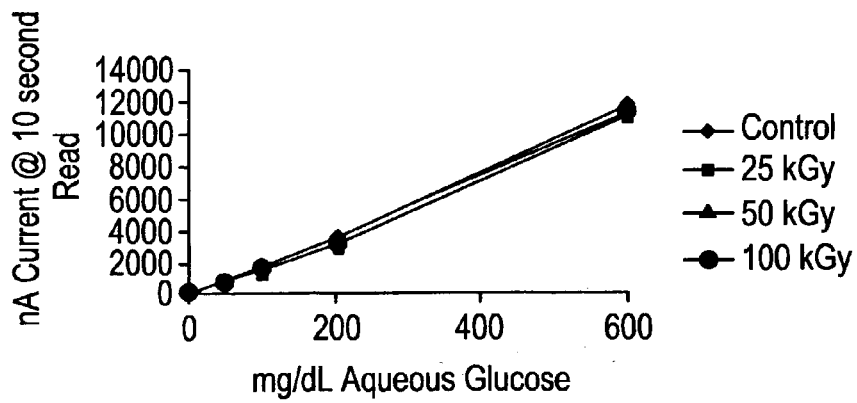
FIGS. 8–12 show plots of current vs. glucose concentration for 5 formulations of PQQ-glucose dehydrogenase/phenothiazine biosensors exposed to varying levels of radiation.
Figure 9:
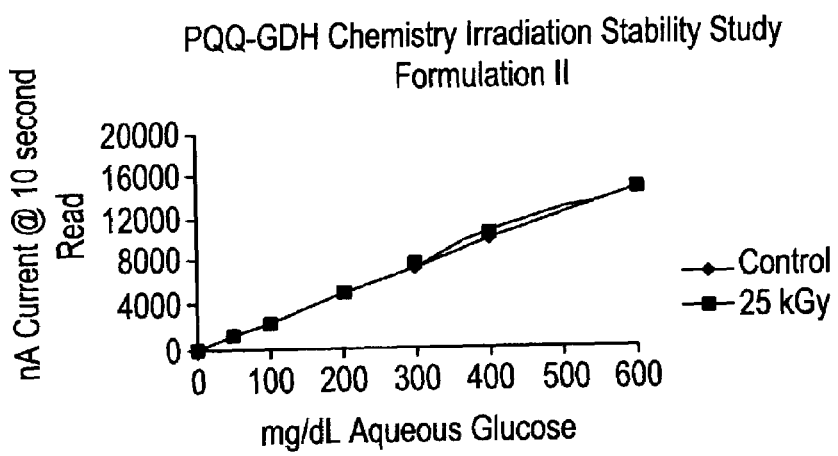
Figure 10:
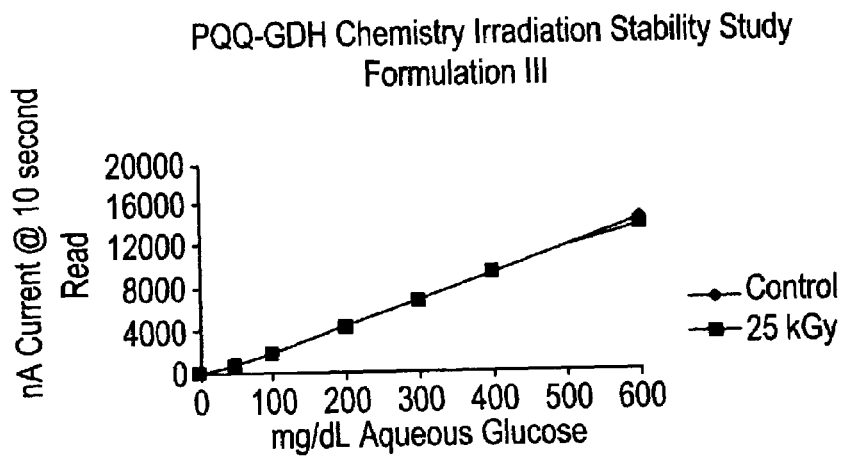
Figure 11:
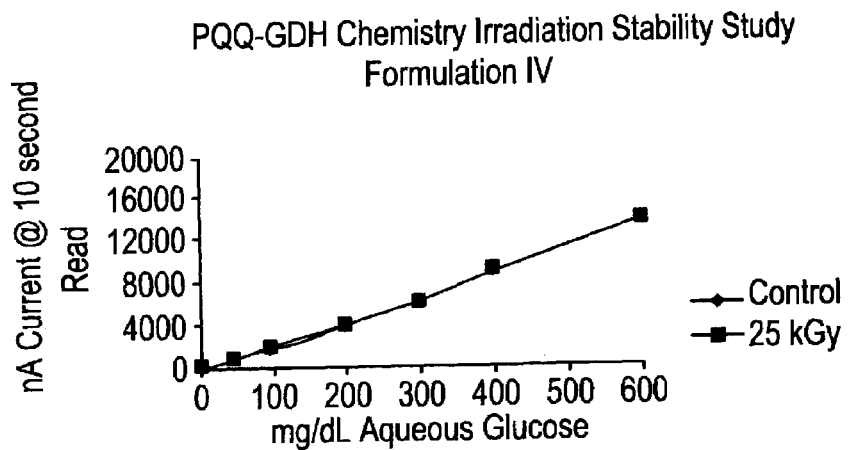
Figure 12:
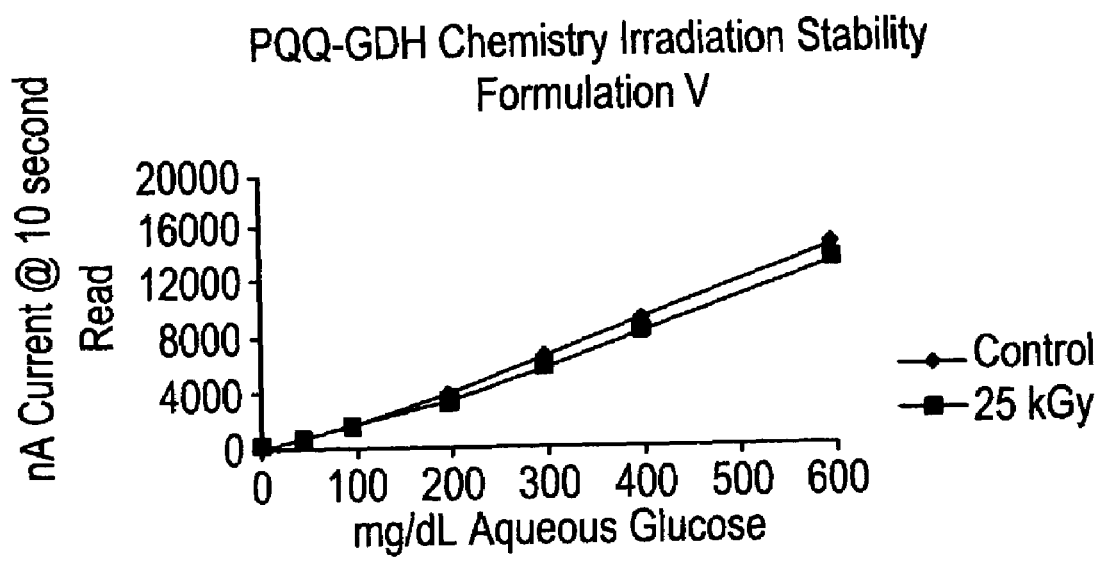

In subsequent tests, the sensors were subjected to the following environmental conditions prior to testing: 1) 50° C. for 2, 4, and 8 weeks; and 2) room temperature with 40% relative humidity. The sensors were poised at a potential of 150 mV relative to the Ag/AgCl reference electrode and the resulting current was measured. This mediator/enzyme combination is quite stable to both heat stress and humidity stress as shown in FIG. 7.

Sterilization of Biosensors and Radiation Stability Data

Five formulations of biosensor reagents (Table 1) were prepared and subjected to E-beam irradiation using Sure-Beam® sterilization technology at Titan Scan Technologies (San Diego, Calif.). Formulation I was irradiated at 25 kGy, 50 kGy, and 100 kGy, whereas each of Formulations II–V was irradiated at 25 kGy only. In the two rightmost column headings of Table 1, the abbreviation CMC refers to carboxymethylcellulose, and the abbreviation PEO refers to polyethylene oxide.

TABLE 1

| Formulation # | Enzyme Concentration PQQ-GDH Units | Concentration Mediator I mM | Polymer Concentration CMC % | Polymer Concentration PEO % |
|---|---|---|---|---|
| I | 20 | 12 | 0 | 0 |
| II | 20 | 12 | 0 | 0 |

TABLE 1-continued

| Formulation # | Enzyme Concentration PQQ-GDH Units | Concentration Mediator I mM | Polymer Concentration CMC % | Polymer Concentration PEO % |
|---|---|---|---|---|
| III | 20 | 12 | 1 | 0 |
| IV | 20 | 12 | 2 | 0 |
| V | 20 | 12 | 0 | 2 |

FIGS. 8–12 show glucose dose response curves for each of the five formulations both before and after irradiation. The stability of the five formulations is high, as clearly shown by the near overlapping of the glucose response generated before and after irradiation.

Table 2 shows the results of enzyme assays conducted on the five formulations both before and after irradiation. Enzyme activity following irradiation remains high in all instances.

TABLE 2

| Formulation # | kGy Level | Enzyme Activity |
|---|---|---|
| I | 0 | 4.67 |
|  | 25 | 4.32 |
|  | 50 | 4.20 |
|  | 100 | 4.24 |
| II | 0 | 3.31 |
|  | 25 | 3.34 |
| III | 0 | 4.93 |
|  | 25 | 4.87 |
| IV | 0 | 4.96 |
|  | 25 | 4.86 |
| V | 0 | 3.63 |
|  | 25 | 4.05 |

The foregoing detailed description and examples have been provided by way of explanation and illustration, and are not intended to limit the scope of the appended claims. Many variations in the presently preferred embodiments illustrated herein be obvious to one of ordinary skill in the art, and remain within the scope of the appended claims and their equivalents.

The invention claimed is:

1. A reagent for detecting an analyte, comprising:
an enzyme selected from the group consisting of a flavoprotein, a quinoprotein, and a combination thereof; and
a mediator selected from the group

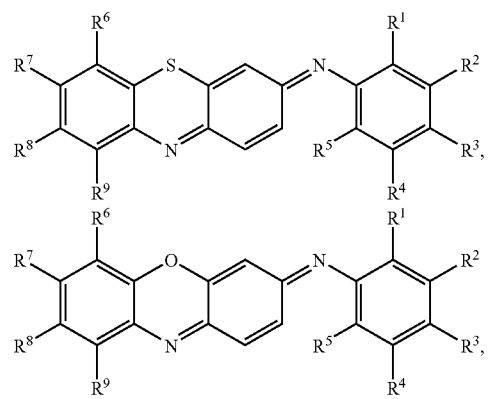

and combinations thereof, wherein $R^1$, $R^2$, $R^3$, $R^4$, $R^5$, $R^6$, $R^7$, $R^8$, and $R^9$ are the same or different, and are independently selected from the group consisting of hydrogen, alkyl, alkenyl, alkynyl, aryl, heteroaryl, cyclic, heterocyclic, halo, haloalkyl, carboxy, carboxyalkyl, alkoxycarbonyl, aryloxycarbonyl, aromatic keto, aliphatic keto, alkoxy, aryloxy, nitro, dialkylamino, aminoalkyl, sulfo, dihydroxyboron, and combinations thereof.

2. The reagent of claim 1, wherein the mediator is selected from the group consisting of 3-(4'-chloro-phenylimino)-3H-phenothiazine, 3-(4'-diethylamino-phenylimino)-3H-phenothiazine, 3-(4'ethyl-phenylimino)-3H-phenothiazine, 3-(4'-trifluoromethyl-phenylimino)-3H-phenothiazine, 3-(4'-methoxycarbonyl-phenylimino)-3H-phenothiazine, 3-(4'-nitro-phenylimino)-3H-phenothiazine, 3-(4'-methoxyphenylimino)-3H-phenothiazine, 7-acetyl-3-(4'-methoxycarbonylphenylimino)-3H-phenothiazine, 7-trifluoromethyl-3-(4'-methoxycarbonylphenylimino)-3H-phenothiazine, 3-(4'-.omega.-carboxy-n-butyl-phenylimino)-3H-phenothiazine, 3-(4'-aminomethyl-phenylimino)-3H-phenothiazine, 3-(4'-(2"-(5"-(p-aminophenyl)-1,3,4-oxadiazoyl)phenylimino)-3H-phenothiazine, 3-(4'-.beta.-aminoethyl-phenylimino)-3H-phenothiazine, 6-(4'-ethylphenyl)amino-3-(4'-ethyl-phenylimino)-3H-phenothiazine, 6-(4'-[2-(2-ethanoloxy)ethoxy]ethoxyphenyl) amino-3-(4'-[2-(2-ethanoloxy)e-thoxy]ethoxy-phenylimino-3H-phenothiazine, 3-(4'-[2-(2-ethanoloxy)ethoxy]e-thoxy-phenylimino-3H-phenothiazine, 3-(4'-phenylimino)-3H-phenothiazinebor-onic acid, (3-(3',5'-dicarboxy-phenylimino)-3H-phenothiazine, 3-(4'-carboxy-phenylimino)-3H-phenothiazine, 3-(3',5'-dicarboxy-phenylimino)-3H-phenoxazine, 3-(3',5'-phenylimino)-3H-phenothiazinedisulfonic acid, 3-(3-phenylimino)-3H-phenothiazinesulfonic acid, and combinations thereof.

3. The reagent of claim 1, wherein the mediator comprises

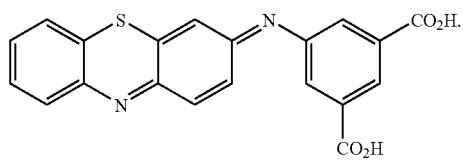

4. The reagent of claim 1, wherein the mediator comprises

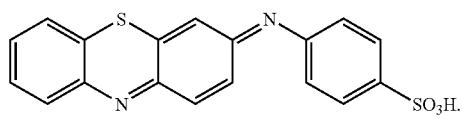

5. The reagent of claim 1, wherein the flavoprotein is selected from the group consisting of FAD-glucose oxidase, flavin-hexose oxidase, FAD-glucose dehydrogenase, [FAD]-lactate oxidase, [FAD]-cholesterol oxidase, [FAD]-alcohol oxidase, [FAD]-d-aminoacid oxidase, [FAD]-choline oxidase, and combinations thereof.

6. The reagent of claim 1, wherein the quinoprotein is selected from the group consisting of PQQ-membrane bound glucose dehydrogenase, PQQ-soluble glucose dehydrogenase, [PQQ]-lactate dehydrogenase, [PQQ]-aldehyde dehydrogenase, [PQQ]-methylamine dehydrogenase, [PQQ]-alcohol dehydrogenase, and combinations thereof.

7. The reagent of claim 1, wherein the enzyme is selected from the group consisting of FAD-glucose oxidase, PQQ-glucose dehydrogenase, and a combination thereof.

8. The reagent of claim 7, wherein the mediator is selected from the group consisting of 3-(4'-chloro-phenylimino)-3H-phenothiazine, 3-(4'-diethylamino-phenylimino)-3H-phenothiazine, 3-(4'ethyl-phenylimino)-3H-phenothiazine, 3-(4'-trifluoromethyl-phenylimino)-3H-phenothiazine, 3-(4'-methoxycarbonyl-phenylimino)-3H-phenothiazine, 3-(4'-nitro-phenylimino)-3H-phenothiazine, 3-(4'-methoxyphenylimino)-3H-phenothiazine, 7-acetyl-3-(4'-methoxycarbonylphenylimino)-3H-phenothiazine, 7-trifluoromethyl-3-(4'-methoxycarbonylphenylimino)-3H-phenothiazine, 3-(4'-.omega.-carboxy-n-butyl-phenylimino)-3H-phenothiazine, 3-(4'-aminomethyl-phenylimino)-3H-phenothiazine, 3-(4'-(2"-(5"-(p-aminophenyl)-1,3,4-oxadiazoyl)phenylimino)-3H-phenothiazine, 3-(4'-.beta.-aminoethyl-phenylimino)-3H-phenothiazine, 6-(4'-ethylphenyl)amino-3-(4'-ethyl-phenylimino)-3H-phenothiazine, 6-(4'-[2-(2-ethanoloxy)ethoxy]ethoxyphenyl) amino-3-(4'-[2-(2-ethanoloxy)e-thoxy]ethoxy-phenylimino-3H-phenothiazine, 3-(4'-[2-(2-ethanoloxy)ethoxy]ethoxy-phenylimino-3H-phenothiazine, 3-(4'-phenylimino)-3H-phenothiazineboronic acid, (3-(3',5'-dicarboxy-phenylimino)-3H-phenothiazine, 3-(4'-carboxy-phenylimino)-3H-phenothiazine, 3-(3',5'-dicarboxy-phenylimino)-3H-phenoxazine, 3-(3',5'-phenylimino)-3H-phenothiazinedisulfonic acid, 3-(3-phenylimino)-3H-phenothiazinesulfonic acid, and combinations thereof.

9. The reagent of claim 7, wherein the mediator comprises

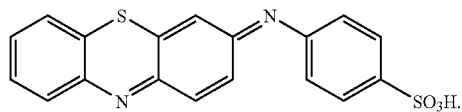

10. The reagent of claim 8 wherein the mediator comprises

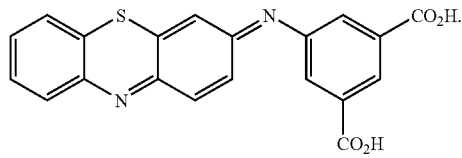

11. The reagent of claim 1, further comprising a polymer selected from the group consisting of carboxymethylcellulose, polyethylene oxide, and combinations thereof.

12. A reagent for detecting glucose, comprising:
PQQ-glucose dehydrogenase in an activity of about 20 Units/µL;
a buffer having a concentration between about 0.1 mM and about 100 mM, and a pH between about 4.5 and about 9.5; and
a mediator having a structure

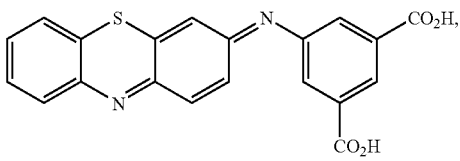

wherein the mediator has a concentration in the buffer between about 0.1 mM and about 30 mM.

13. The reagent of claim 12, wherein the buffer is selected from the group consisting of sodium phosphate, potassium phosphate, Hepes, MOPS, TES, Pipes, ACES, BES, Dulbecco's, and combinations thereof.

14. The reagent of claim 12, wherein the buffer comprises sodium phosphate.

15. The reagent of claim 12, further comprising a polymer selected from the group consisting of carboxymethylcellulose, polyethylene oxide, and combinations thereof.

16. A reagent for detecting an analyte, comprising:
an enzyme selected from the group consisting of PQQ-glucose dehydrogenase, FAD-glucose oxidase, and a combination thereof; and
a mediator selected from the group consisting of

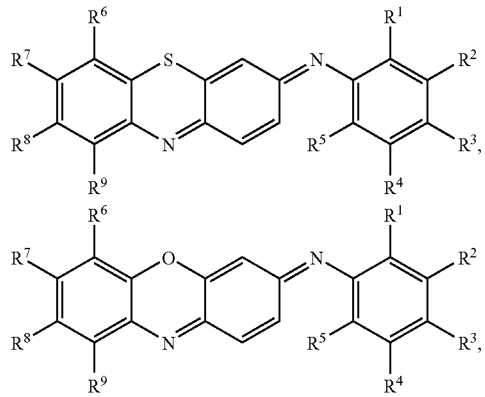

and combinations thereof,
wherein $R^1$, $R^2$, $R^3$, $R^4$, $R^5$, $R^6$, $R^7$, $R^8$, and $R^9$ are the same or different, and are independently selected from the group consisting of hydrogen, alkyl, alkenyl, alkynyl, aryl, heteroaryl, cyclic, heterocyclic, halo, haloalkyl, carboxy, carboxyalkyl, alkoxycarbonyl, aryloxycarbonyl, aromatic keto, aliphatic keto, alkoxy, aryloxy, nitro, dialkylamino, aminoalkyl, sulfo, dihydroxyboron, and combinations thereof.

17. The reagent of claim 16, wherein the mediator comprises

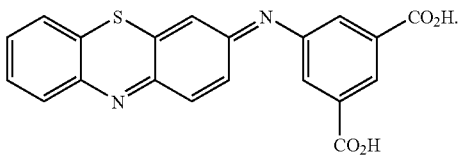

18. The reagent of claim 16, wherein the mediator comprises

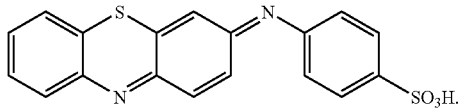

19. An electrochemical sensor comprising:
a working electrode having a surface; and
a second electrode coupled to the working electrode,
wherein the surface of the working electrode is coated with a solution of a reagent comprising an enzyme selected from the group consisting of a flavoprotein, a quinoprotein, and a combination thereof; and a mediator selected from and combinations thereof,

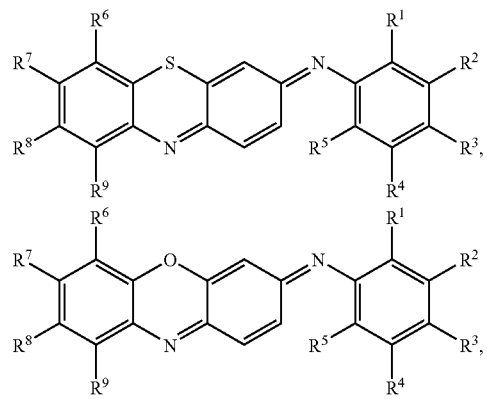

wherein $R^1$, $R^2$, $R^3$, $R^4$, $R^5$, $R^6$, $R^7$, $R^8$, and $R^9$ are the same or different, and are independently selected from the group consisting of hydrogen, alkyl, alkenyl, alkynyl, aryl, heteroaryl, cyclic, heterocyclic, halo, haloalkyl, carboxy, carboxyalkyl, alkoxycarbonyl, aryloxycarbonyl, aromatic keto, aliphatic keto, alkoxy, aryloxy, nitro, dialkylamino, aminoalkyl, sulfo, dihydroxyboron, and combinations thereof.

20. The electrochemical sensor of claim 19, wherein the working electrode is selected from the group consisting of a carbon electrode, a platinum electrode, a palladium electrode, and a gold electrode.

21. The electrochemical sensor of claim 19, wherein the second electrode is selected from the group consisting of a reference electrode and a quasi-reference electrode.

22. The electrochemical sensor of claim 19, wherein the second electrode is a silver/silver chloride reference electrode.

23. The electrochemical sensor of claim 19, wherein the surface of the working electrode has an area of about 0.00113 cm$^2$.

24. An electrochemical sensor comprising:
a working electrode having a surface; and
a reference electrode coupled to the working electrode,
wherein the surface of the working electrode is coated with a solution of a reagent comprising
PQQ-glucose dehydrogenase in an activity of about 1 Units/μL to about 100 Units/μL;
a buffer having a concentration of about 100 mM and a pH of about 7.4; and
a mediator having a structure

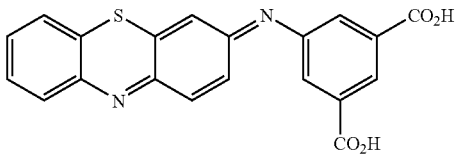

wherein the mediator has a concentration in the buffer of about 1 mM to about 100 mM.

25. The electrochemical sensor of claim 24, wherein the activity of the PQQ-glucose dehydrogenase is about 20 Units/μL, and wherein the concentration of the mediator in the buffer is about 24 mM.

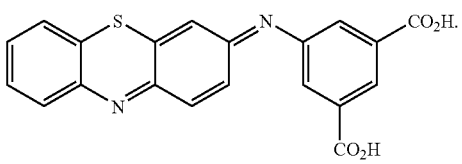

26. The electrochemical sensor of claim 24, wherein the activity of the PQQ-glucose dehydrogenase is about 10 Units/μL, and wherein the concentration of the mediator in the buffer is about 12 mM.

27. The reagent of claim 24, further comprising a polymer selected from the group consisting of carboxymethylcellulose, polyethylene oxide, and combinations thereof.

28. A device for measuring an analyte, comprising:
a lancet; and
a sampling chamber connected to the lancet, comprising:
a reagent comprising:
an enzyme selected from the group consisting of PQQ-glucose dehydrogenase, FAD-glucose oxidase, and a combination thereof; and
a mediator selected from

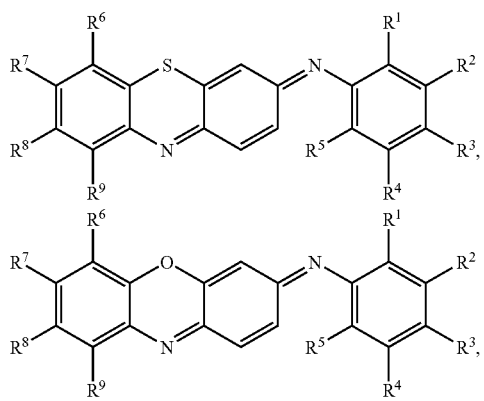

and combinations thereof, wherein $R^1$, $R^2$, $R^3$, $R^4$, $R^5$, $R^6$, $R^7$, $R^8$, and $R^9$ are the same or different, and are independently selected from the group consisting of hydrogen, alkyl, alkenyl, alkynyl, aryl, heteroaryl, cyclic, heterocyclic, halo, haloalkyl, carboxy, carboxyalkyl, alkoxycarbonyl, aryloxycarbonyl, aromatic keto, aliphatic keto, alkoxy, aryloxy, nitro, dialkylamino, aminoalkyl, sulfo, dihydroxyboron, and a combination thereof.

29. The device of claim 28, wherein the mediator is selected from the group consisting of 3-(4'-chloro-phenylimino)-3H-phenothiazine, 3-(4'-diethylamino-phenylimino)-3H-phenothiazine, 3-(4'ethyl-phenylimino)-3H-phenothiazine, 3-(4'-trifluoromethyl-phenylimino)-3H-phenothiazine, 3-(4'-methoxycarbonyl-phenylimino)-3H-phenothiazine, 3-(4'-nitro-phenylimino)-3H-phenothiazine, 3-(4'-methoxy-phenylimino)-3H-phenothiazine, 7-acetyl-3'-(4'-methoxycarbonylphenylimino)-3H-phenothiazine, 7-trifluoromethyl-3-(4'-methoxycarbonylphenylimino)-3H-phenothiazine, 3-(4'-.omega.-carboxy-n-butyl-phenylimino)-3H-phenothiazine, 3-(4'-aminomethyl-phenylimino)-3H-phenothiazine, 3-(4'-(2''-(5''-(p-aminophenyl)-1,3,4-oxadiazoyl)phenylimino)-3H-phenothiazine, 3-(4'-.beta.-aminoethyl-phenylimino)-3H-phenothiazine, 6-(4'-ethylphenyl)amino-3-(4'-ethyl-phenylimino)-3H-phenothiazine, 6-(4'-[2-(2-ethanoloxy)ethoxy]ethoxyphenyl)amino-3-(4'-[2-(2-ethanoloxy)ethoxy]ethoxy-phenylimino-3H-phenothiazine, 3-(4'-[2-(2-ethanoloxy)ethoxy]ethoxy-phenylimino-3H-phenothiazine, 3-(4'-phenylimino)-3H-phenothiazineboronic acid, (3-(3',5'-dicarboxy-phenylimino)-3H-phenothiazine, 3-(4'-carboxy-phenylimino)-3H-phenothiazine, 3-(3',5'-dicarboxy-phenylimino)-3H-phenoxazine, 3-(3',5'-phenylimino)-3H-phenothiazinedisulfonic acid, 3-(3-phenylimino)-3H-phenothiazinesulfonic acid, and combinations thereof.

30. The device of claim 28, wherein the mediator comprises

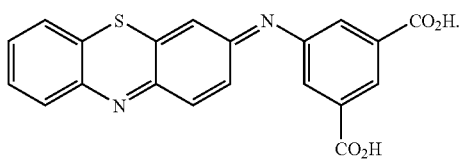

31. The device of claim 28, wherein the mediator comprises

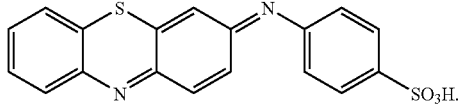

32. A method for detecting an analyte which undergoes a chemical reaction, the method comprising:
providing an electrode surface;
catalyzing the chemical reaction with an enzyme selected from the group consisting of a flavoprotein, a quinoprotein, and a combination thereof;
generating a redox equivalent by the chemical reaction; and transferring the redox equivalent to the electrode surface using a mediator selected from

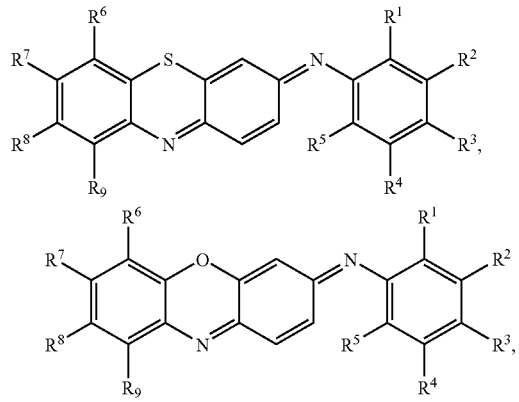

and a combination thereof, wherein $R^1$, $R^2$, $R^3$, $R^4$, $R^5$, $R^6$, $R^7$, $R^8$, and $R^9$ are the same or different, and are independently selected from the group consisting of hydrogen, alkyl, alkenyl, alkynyl, aryl, heteroaryl, cyclic, heterocyclic, halo, haloalkyl, carboxy, carboxyalkyl, alkoxycarbonyl, aryloxycarbonyl, aromatic keto, aliphatic keto, alkoxy, aryloxy, nitro, dialkylamino, aminoalkyl, sulfo, dihydroxyboron, and combinations thereof.

33. The method of claim 32, wherein the analyte is glucose.

34. The method of claim 32, wherein the mediator is selected from the group consisting of 3-(4'-chloro-phenylimino)-3H-phenothiazine, 3-(4'-diethylamino-phenylimino)-3H-phenothiazine, 3-(4'ethyl-phenylimino)-3H-phenothiazine, 3-(4'-trifluoromethyl-phenylimino)-3H-phenothiazine, 3-(4'-methoxycarbonyl-phenylimino)-3H-phenothiazine, 3-(4'-nitro-phenylimino)-3H-phenothiazine, 3-(4'-methoxy-phenylimino)-3H-phenothiazine, 7-acetyl-3-(4'-methoxycarbonylphenylimino)-3H-phenothiazine, 7-trifluoromethyl-3-(4'-methoxycarbonylphenylimino)-3H-phenothiazine, 3-(4'-.omega.-carboxy-n-butyl-phenylimino)-3H-phenothiazine, 3-(4'-aminomethyl-phenylimino)-3H-phenothiazine, 3-(4'-(2"-(5"-(p-aminophenyl)-1,3,4-oxadiazoyl)phenylimino)-3H-phenothiazine, 3-(4'-.beta.-aminoethyl-phenylimino)-3H-phenothiazine, 6-(4'-ethylphenyl)amino-3-(4'-ethyl-phenylimino)-3H-phenothiazine, 6-(4'-[2-(2-ethanoloxy)ethoxy]ethoxyphenyl)amino-3-(4'-[2-(2-ethanoloxy)ethoxy]ethoxy-phenylimino-3H-phenothiazine, 3-(4'-[2-(2-ethanoloxy)ethoxy] ethoxy-phenylimino-3H-phenothiazine, 3-(4'-phenylimino)-3H-phenothiazinebor-onic acid, (3-(3',5'-dicarboxy-phenylimino)-3H-phenothiazine, 3-(4'-carboxy-phenylimino)-3H-phenothiazine, 3-(3',5'-dicarboxy-phenylimino)-3H-phenoxazine, 3-(3',5'-phenylimino)-3H-phenothiazinedisulfonic acid, 3-(3-phenylimino)-3H-phenothiazinesulfonic acid, and combinations thereof.

35. The method of claim 32, wherein the mediator comprises

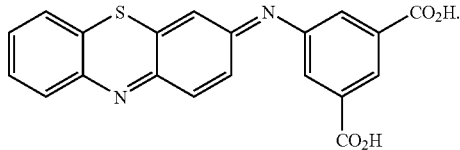

36. The method of claim 32, wherein the flavoprotein is selected from the group

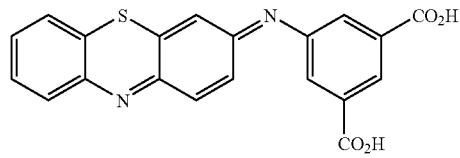

consisting of FAD-glucose oxidase, FAD-glucose dehydrogenase, lactate oxidase, cholesterol oxidase, alcohol oxidase, d-aminoacid oxidase, choline oxidase, and combinations thereof.

37. The method of claim 32, wherein the quinoprotein is selected from the group consisting of PQQ-glucose dehydrogenase, lactate dehydrogenase, aldehyde dehydrogenase, methylamine dehydrogenase, alcohol dehydrogenase, and combinations thereof.

38. The method of claim 32, wherein the enzyme is selected from the group consisting of FAD-glucose oxidase, PQQ-glucose dehydrogenase, and a combination thereof.

39. The method of claim 38, wherein the mediator comprises

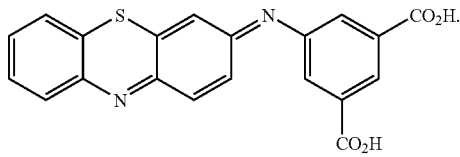

40. The method of claim 38, wherein the mediator comprises

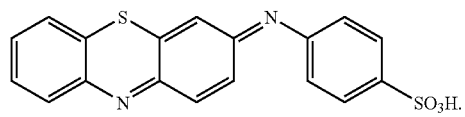

* * * * *